(12) United States Patent
Kruger et al.

(10) Patent No.: US 10,495,567 B2
(45) Date of Patent: Dec. 3, 2019

(54) PHOTOACOUSTIC APPARATUS

(71) Applicant: CANON KABUSHIKI KAISHA, Tokyo (JP)

(72) Inventors: Robert A. Kruger, Oriental, NC (US); Takeshi Sekiya, Kawasaki (JP); Kenji Oyama, Tokyo (JP); Kazuhito Oka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/310,082

(22) PCT Filed: May 12, 2015

(86) PCT No.: PCT/JP2015/002414
§ 371 (c)(1),
(2) Date: Nov. 9, 2016

(87) PCT Pub. No.: WO2015/174085
PCT Pub. Date: Nov. 19, 2015

(65) Prior Publication Data
US 2017/0234790 A1    Aug. 17, 2017

Related U.S. Application Data

(60) Provisional application No. 61/992,983, filed on May 14, 2014.

(51) Int. Cl.
*G01N 21/17* (2006.01)
*A61B 5/00* (2006.01)
*G01N 29/24* (2006.01)

(52) U.S. Cl.
CPC ....... *G01N 21/1702* (2013.01); *A61B 5/0095* (2013.01); *G01N 29/2418* (2013.01);
(Continued)

(58) Field of Classification Search
CPC ....... G01N 21/1702; G01N 2021/1706; G01N 29/26; A61B 5/0095; A61B 8/406;
(Continued)

(56) References Cited

U.S. PATENT DOCUMENTS 5,713,356 A * 2/1998 Kruger ............... A61B 5/0091
600/407
6,403,944 B1 * 6/2002 MacKenzie .......... A61B 5/0095
250/214.1
(Continued)

FOREIGN PATENT DOCUMENTS

CN    102596046 A    7/2012
CN    103354731 A    10/2013
(Continued)

OTHER PUBLICATIONS https://en.wikipedia.org/wiki/Beer%E2%80%93Lambert_law.*

*Primary Examiner* — Mohamed K Amara
(74) *Attorney, Agent, or Firm* — Canon U.S.A., Inc. IP Division (57) ABSTRACT

A photoacoustic apparatus includes a light irradiation unit configured to irradiate a subject with light a plurality of times; a driving unit configured to move a supporting member so that relative positions of the supporting member and the subject differ at each of the plurality of times; a plurality of transducers configured to receive acoustic waves generated through the plurality of times of irradiation and output a plurality of groups of reception signals corresponding to the plurality of times of irradiation; the supporting member configured to support the transducers such that directional axes of at least some of the transducers converge; a first memory configured to store the groups of reception signals; and a processing unit configured to obtain subject information at a target position by assigning, to each of the
(Continued)

groups of reception signals, a weight corresponding to relative positions of the supporting member and the target position.

25 Claims, 6 Drawing Sheets

(52) U.S. Cl.
CPC ............... *G01N 2021/1706* (2013.01); *G01N 2021/1708* (2013.01)

(58) Field of Classification Search
CPC ..... A61B 8/4209; A61B 8/429; A61B 8/4444; A61B 8/5215; A61B 8/0825; A61B 8/15; A61B 8/4494; A61B 8/587; A61B 5/0073; A61B 5/7257; A61B 8/00; A61B 8/08; G01S 15/8977; G01S 15/8993
See application file for complete search history.

(56) References Cited

U.S. PATENT DOCUMENTS

| | | | | |
|---|---|---|---|---|
| 9,445,786 B2* | 9/2016 | Zalev | ..................... | A61B 8/52 |
| 9,572,497 B2* | 2/2017 | Razansky | ............ | A61B 5/0073 |
| 9,723,995 B2* | 8/2017 | Boctor | ................ | A61B 5/0095 |
| 9,766,211 B2* | 9/2017 | Oishi | ................... | A61B 5/0095 |
| 9,833,187 B2* | 12/2017 | Eyal | ..................... | A61B 5/0095 |
| 9,901,257 B2* | 2/2018 | Tokita | .................. | A61B 5/0095 |
| 2003/0159498 A1* | 8/2003 | Small | ....................... | G01H 3/00 |
| | | | | 73/24.02 |
| 2004/0220465 A1* | 11/2004 | Cafarella | ............ | A61B 5/0091 |
| | | | | 600/407 |
| 2005/0175540 A1* | 8/2005 | Oraevsky | ............. | A61B 5/0095 |
| | | | | 424/9.5 |
| 2008/0173093 A1* | 7/2008 | Wang | ................... | A61B 5/0073 |
| | | | | 73/602 |
| 2011/0112391 A1* | 5/2011 | Nishihara | ........... | A61B 5/0059 |
| | | | | 600/407 |
| 2011/0184260 A1* | 7/2011 | Robinson | .......... | A61B 5/14532 |
| | | | | 600/316 |
| 2012/0116204 A1* | 5/2012 | Steenbergen | ........ | A61B 5/0095 |
| | | | | 600/407 |
| 2013/0210058 A1* | 8/2013 | White | ................... | A61B 5/1171 |
| | | | | 435/29 |
| 2014/0155760 A1* | 6/2014 | Ridder | ................ | A61B 5/1171 |
| | | | | 600/479 |
| 2014/0171759 A1* | 6/2014 | White | ................... | A61B 5/6835 |
| | | | | 600/306 |
| 2014/0303463 A1* | 10/2014 | Robinson | .......... | A61B 5/14552 |
| | | | | 600/316 |
| 2015/0223903 A1* | 8/2015 | Bell | ..................... | A61B 5/0095 |
| | | | | 600/424 |
| 2015/0359478 A1* | 12/2015 | Eyal | ................... | A61B 5/0095 |
| | | | | 600/437 |
| 2016/0213256 A1* | 7/2016 | Li | ........................ | A61B 5/0095 |
| 2017/0209119 A1* | 7/2017 | Masaki | .............. | A61B 5/0095 |
| 2017/0231602 A1* | 8/2017 | Venkataraman | ....... | A61B 8/085 |
| | | | | 600/431 |
| 2017/0265748 A1* | 9/2017 | Nanaumi | ............. | A61B 5/0095 |
| 2018/0064347 A1* | 3/2018 | Adair | .................. | A61B 5/0095 |

FOREIGN PATENT DOCUMENTS

| | | | |
|---|---|---|---|
| EP | 2623022 A1 | 8/2013 | |
| JP | 2012-179348 A | 9/2012 | |
| JP | 2013215236 A | 10/2013 | |
| WO | WO-2010024290 A1 * | 3/2010 | ........... A61B 5/0059 |
| WO | 2011/062125 A1 | 5/2011 | |
| WO | 2012/108172 A1 | 8/2012 | |

* cited by examiner

PHOTOACOUSTIC APPARATUS

TECHNICAL FIELD

The present invention relates to a photoacoustic apparatus for obtaining subject information by using a photoacoustic effect.

BACKGROUND ART

In the medical field, studies are being carried out into photoacoustic apparatuses that irradiate a subject with light, receive acoustic waves generated in the subject due to the light, and analyze the acoustic waves to form an image representing information about the subject.

PTL 1 describes a photoacoustic apparatus that performs photoacoustic imaging by using a probe in which transducers are arranged on a hemisphere. With this probe, photoacoustic waves generated in a specific region can be received with high sensitivity. Thus, the resolution of subject information in the specific region is high. Also, PTL 1 describes a technique in which scanning is performed on a certain plane by using the probe, and the probe receives acoustic waves at a plurality of positions so as to obtain reception signals. Also, PTL 1 describes a technique in which reconstruction is performed after obtaining the reception signals at the plurality of positions.

CITATION LIST

Patent Literature

PTL 1: Japanese Patent Laid-Open No. 2012-179348

SUMMARY OF INVENTION

In the method of performing reconstruction after obtaining reception signals at a plurality of positions described in PTL 1, there is a probability that a region exists where the quantitativity of obtained subject information is low.

A photoacoustic apparatus disclosed in this description includes a light irradiation unit; a plurality of transducers configured to receive acoustic waves generated through irradiation of a subject with light emitted from the light irradiation unit and output a group of reception signals; a supporting member configured to support the plurality of transducers such that directional axes of at least some of the plurality of transducers converge; a driving unit configured to move at least one of the supporting member and the subject; a first memory configured to store the group of reception signals output from the plurality of transducers; and a processing unit configured to obtain subject information at a target position of the subject. The light irradiation unit irradiates the subject with light a plurality of times. The driving unit moves the supporting member so that relative positions of the supporting member and the subject differ at each of the plurality of times of light irradiation. The plurality of transducers receive acoustic waves generated through the plurality of times of light irradiation and output a plurality of groups of reception signals corresponding to the plurality of times of light irradiation. The first memory stores the plurality of groups of reception signals. The processing unit obtains the subject information at the target position by assigning, to each of the plurality of groups of reception signals stored in the first memory, a weight corresponding to relative positions of the supporting member and the target position.

DESCRIPTION OF EMBODIMENTS

First Embodiment

A photoacoustic apparatus according to a first embodiment obtains subject information on the basis of reception signals of photoacoustic waves. Subject information according to this embodiment is information about a subject, which is obtained from reception signals of photoacoustic waves generated by a photoacoustic effect. Specifically, subject information represents a generated sound pressure (initial sound pressure), a light energy absorption density, a light absorption coefficient, a concentration of a substance constituting a tissue, and so forth. Here, a concentration of a substance is, for example, oxygen saturation, oxyhemoglobin concentration, deoxyhemoglobin concentration, and total hemoglobin concentration. The total hemoglobin concentration is the sum of oxyhemoglobin concentration and deoxyhemoglobin concentration.

In this embodiment, a description will be given of a photoacoustic apparatus provided with a probe that includes a plurality of transducers arranged such that axes along a direction of the highest reception sensitivity (hereinafter referred to as "directional axes") converge. That is, a description will be given of a case where a plurality of transducers are arranged so that acoustic waves generated in a certain region where the directional axes converge can be received with high sensitivity. The photoacoustic apparatus according to this embodiment changes the relative positions of a subject and the probe, which receives acoustic waves a plurality of times. Also, the photoacoustic apparatus stores, in a memory, a group of time-series reception signals output from the probe as reception signal data. Also, the photoacoustic apparatus according to this embodiment obtains subject information at individual target positions in a region of interest (ROI) by using the reception signal data that has been obtained through a plurality of times of reception of acoustic waves and stored in the memory. A target position is a pixel in a case where a two-dimensional ROI is set, and is a voxel in a case where a three-dimensional ROI is set. In this description, a plurality of time-series signals output from the plurality of transducers in response to one irradiation with light when the probe and a subject have a certain relative positional relationship are referred to as "a group of reception signals". On the other hand, groups of reception signals output from the plurality of transducers in response to a plurality of times of irradiation with light in a plurality of states where the relative positional relationship between the probe and a subject differs are referred to as "a plurality of groups of reception signals".

In a case where subject information is obtained by using a group of reception signals that have been obtained by receiving acoustic waves when the probe according to this embodiment is at a position, the resolution of the subject information is typically the highest at a certain position where directional axes converge. The resolution of the subject information has a tendency to decrease with increasing distance from the certain position. In this case, it is estimated that the probe is able to receive, with relatively high sensitivity, acoustic waves generated in a certain region ranging from a position where the resolution is the highest to a position where the resolution is half the highest resolution. In this embodiment, the region ranging from the position where the resolution is the highest to the position where the resolution is half the highest resolution is referred to as a "highly-sensitive region".

In this embodiment, a plurality of groups of reception signals that have been obtained over a plurality of times from the following point of view are weighted, and thereby subject information at a target position is obtained.

A large weight may be assigned to a reception signal output from a transducer oriented to the target position. Accordingly, the weight of a reception signal output from the transducer that has received, with high sensitivity, photoacoustic waves generated at the target position can be increased, and thus the weight of a reception signal having a high S/N ratio can be increased. As a result, the S/N ratio of subject information at the target position reconstructed by using such a weighted reception signal can also be increased. That is, the quantitativity and resolution of subject information at the target position can be increased. Further, with such weighting being applied to all target positions, the quantitativity and resolution at all positions of a reconstructed image can be increased.

As described above, the individual transducers arranged in the probe according to this embodiment are able to receive acoustic waves generated in a highly-sensitive region with high sensitivity. Thus, a larger weight may be assigned to a group of reception signals obtained by the probe when the highly-sensitive region is closer to a target position, among a plurality of groups of reception signals stored in the memory. That is, a weight to be assigned to a group of reception signals obtained by the probe may be determined in accordance with the relative positions of the target position and the probe. Accordingly, a large weight can be assigned to a group of reception signals estimated to have been received with high sensitivity.

According to this embodiment, the quantitativity and resolution at individual target positions can be easily increased by uniformly determining a weight for the reception signals output from the individual transducers when the target position and the probe have a certain relative positional relationship.

According to this embodiment, the amount of calculation for determining a weight can be reduced compared to the case of calculating weights for individual transducers in accordance with the relative positions of the individual transducers and the target position.

Now, the following case is discussed in which weights calculated in advance are stored in a memory and weighting is performed by reading a weight from the memory. In this case, according to this embodiment, weights for individual relative positions of the individual transducers and a target position are not stored, and it is sufficient to store a weight corresponding to the relative positions of the probe and the target position. Therefore, according to this embodiment, the amount of data of weights can be reduced, and accordingly the capacity of the memory for storing the data of weights can be reduced.

The photoacoustic apparatus according to this embodiment is able to arbitrarily assign a weight to a group of reception signals stored in the memory, and is thus able to change the weight to be assigned to the signals in accordance with a purpose after receiving the signals.

In a case where a sound source exists at a target position, acoustic waves isotropically propagate in all directions from the target position. Thus, the transducers may be positioned so as to be able to receive many frequency components of the acoustic waves generated at the target position. Accordingly, at the time of reconstructing an image, the energy corresponding to a reconstruction artifact is distributed over the entire reconstructed image, and thus local occurrence of a reconstruction artifact can be suppressed.

Further, almost the same weight may be assigned to reception signals output from the transducers at the point-symmetrical positions with the target position at the center. Accordingly, a reconstruction artifact is likely to appear point-symmetrically with the target position at the center. As a result, the energy corresponding to the reconstruction artifact is distributed over the entire reconstructed image more evenly, and thus local occurrence of a reconstruction artifact can be suppressed more.

Further, a weight may be assigned to reception signals at individual target positions in an ROI from the above-described point of view. Accordingly, at each target position in the ROI, the contrast between a reconstructed image at the target position (signal component) and a reconstruction artifact (noise component) increases.

Thus, particularly in a case where highly-sensitive regions exist at the equal distance from a target position, the same weight may be assigned to the individual transducers arranged in the probe. Further, the photoacoustic apparatus according to this embodiment assigns, from the above-described point of view, a weight to a plurality of groups of reception signals that have been obtained by moving the plurality of transducers that are arranged so as to be able to receive acoustic waves generated in a highly-sensitive region with high sensitivity. Accordingly, at each target position in the ROI, the contrast between a reconstructed image at the target position (signal component) and a reconstruction artifact (noise component) increases, and the resolution increases.

Hereinafter, embodiments of the present invention will be described in detail with reference to the drawings. Basically, the same elements are denoted by the same reference numerals, and the description thereof is not repeated.

System Configuration

Figure 1:
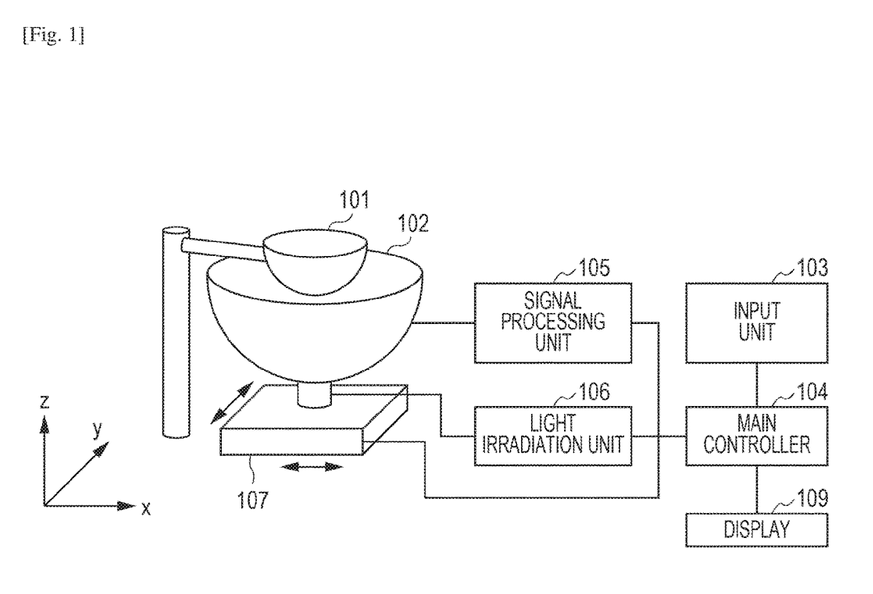
FIG. 1 is a diagram illustrating the configuration of a photoacoustic apparatus according to a first embodiment.

The configuration of the photoacoustic apparatus according to the first embodiment will be described with reference to FIG. 1. For the convenience of description, a certain horizontal axis is referred to as an x-axis, a horizontal axis perpendicular to the x-axis is referred to as a y-axis, and an axis perpendicular to the x- and y-axes is referred to as a z-axis.

The photoacoustic apparatus according to the first embodiment includes a holding cup 101, a probe 102, an input unit 103, a main controller 104, a signal processing unit 105, a light irradiation unit 106, a driving device 107, and a display 109.

Hereinafter, these elements will be described.

Holding Cup 101

The holding cup 101 is used to fix a subject so that the subject is not moved during image capturing, and is a hemispherical cup made of a synthetic resin. Alternatively, the holding cup 101 may be made of a thin film of latex rubber or the like as long as the subject can be fixed. The holding cup 101 may be made of a material having a high transmittance for light so as to suppress attenuation of pulsed light applied to the subject. Further, the holding cup 101 may be made of a material having an acoustic impedance similar to the acoustic impedance of a subject so as to reduce reflection of acoustic waves at the interface of the subject.

Probe 102

The probe 102 is constituted by a plurality of transducers 201 and a supporting member 202 for supporting the plurality of transducers 201. The supporting member 202 according to this embodiment is a hemispherical casing in which the plurality of transducers 201 are arranged.

The transducers 201 may be made of a piezoelectric ceramic material represented by lead zirconate titanate (PZT), a high polymer piezoelectric film material represented by polyvinylidene fluoride (PVDF), or the like. An element other than a piezoelectric element may be used. For example, a capacitive micro-machined ultrasonic transducer (cMUT), a transducer using a Fabry-Perot interferometer, or the like may be used.

Figure 2A:
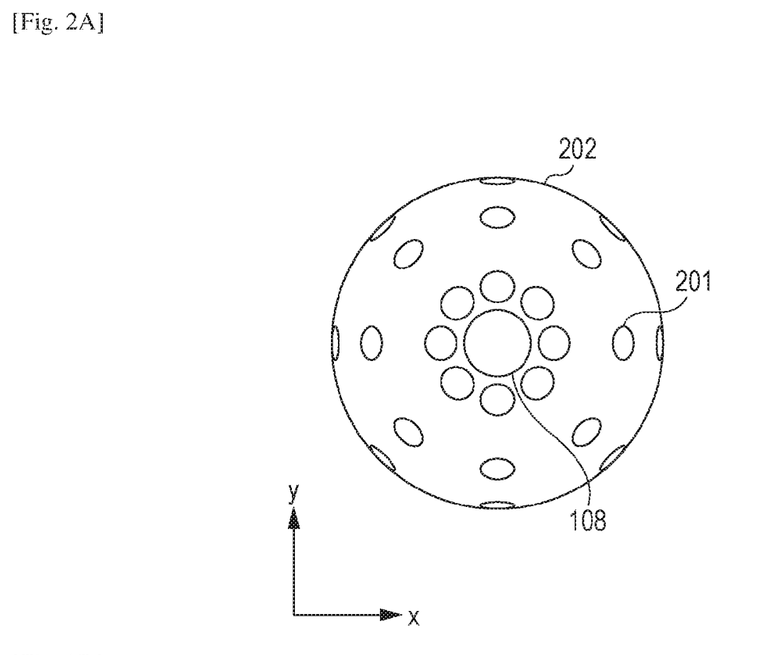
FIG. 2A is a diagram illustrating an arrangement of transducers according to the first embodiment.

Now, an example of arrangement of the transducers 201 in the supporting member 202 will be described with reference to FIGS. 2A and 2B. FIG. 2A is a diagram illustrating the supporting member 202 viewed from the z-axis direction, and FIG. 2B is a diagram illustrating the supporting member 202 viewed from the y-axis direction.

The supporting member 202 supports the plurality of transducers 201 that are radially arranged on the inner surface of the hemisphere. The manner of arrangement is not limited thereto. For example, the transducers 201 may be spirally arranged. A light exit 108 is provided at a bottom portion (pole) of the hemispherical supporting member 202. The inner side of the supporting member 202 may be filled with an acoustic matching material.

Figure 2B:
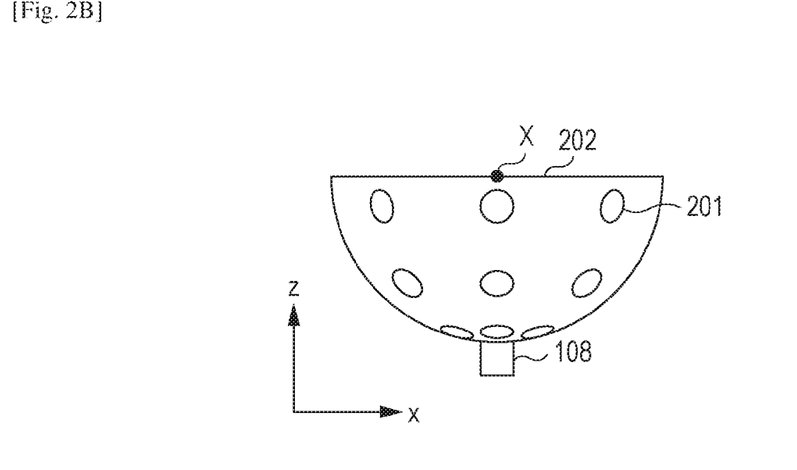
FIG. 2B is a diagram illustrating an arrangement of transducers according to the first embodiment.

In this embodiment, the plurality of transducers 201 are arranged along the hemispherical surface as illustrated in FIGS. 2A and 2B. A point X indicates the curvature center of the hemispherical supporting member 202. The supporting member 202 supports the plurality of transducers 201 such that the directional axes of the transducers 201 converge. That is, the position of the curvature center of the supporting member 202 and the position at which the directional axes of the plurality of transducers 201 converge can be estimated on the basis of the position of the supporting member 202. With the directional axes of the plurality of transducers 201 converged near the curvature center of the hemispherical shape, a region that can be visualized with high accuracy is formed around the curvature center. In this description, such a region that can be visualized with high accuracy is referred to as a highly-sensitive region. With the supporting member 202 being moved relative to a subject by using the driving device 107 (described below), a highly-sensitive region is moved and a wide range of subject information can be visualized with high accuracy.

The highly-sensitive region can be considered as a substantially spherical region having a radius $d_{th}$ expressed by Equation (1), with the curvature center at which a maximum resolution $R_H$ is obtained being the center.

[Math. 1]

$$d_{th} = \frac{r_0}{\phi_d} \cdot R \qquad \text{Equation (1)}$$

Here, R represents the minimum resolution of a highly-sensitive region G, $r_0$ represents the radius of the hemispherical supporting member 202, and $\phi_d$ represents the diameter of the transducer 201. R may be, for example, half of the maximum resolution that can be obtained at the curvature center. In a case where a highly-sensitive region has a substantially spherical shape with the curvature center of the probe being the center, the range of the highly-sensitive region at each position that is two-dimensionally scanned by the probe can be estimated on the basis of the spherical shape and the position of the probe (that is, the curvature center) by using Equation (1).

In this embodiment of the present invention, the arrangement of the plurality of transducers 201 is not limited to the example of the hemispherical shape illustrated in FIGS. 2A and 2B. Any arrangement may be adopted as long as the directional axes of the plurality of transducers 201 converge so as to form a desired highly-sensitive region. That is, any arrangement may be adopted as long as the plurality of transducers 201 are arranged along a curved surface so as to form a desired highly-sensitive region. In this description, a curved surface includes a surface of a perfect sphere and a surface of a hemisphere having an opening. Also, a curved surface includes an uneven surface that can be regarded as a spherical surface, and a surface of an ellipsoid (a shape formed by expanding an ellipse into a three dimensional shape, the surface of which is formed of a quadric surface) that can be regarded as a spherical surface.

Also, in a case where a plurality of transducers are arranged along a supporting member that has a shape formed by cutting a sphere along a certain cross section, the directional axes of the transducers converge the most at the curvature center of the shape of the supporting member. The hemispherical supporting member 202 described in this embodiment is also an example of a supporting member having a shape formed by cutting a sphere along a certain cross section. In this description, such a shape formed by cutting a sphere along a certain cross section is referred to as "a shape based on a sphere". The plurality of transducers supported by the supporting member having such a shape based on a sphere are supported on the spherical surface.

The directional axes of the individual transducers do not necessarily cross one another as long as a desired highly-sensitive region can be formed. It is sufficient that the directional axes of at least some of the plurality of transducers 201 supported by the supporting member 202 converge in a specific region so that photoacoustic waves generated in the specific region can be received with high sensitivity. That is, it is sufficient that the plurality of transducers 201 are arranged on the supporting member 202 so that at least some of the plurality of transducers 201 are able to receive photoacoustic waves generated in a highly-sensitive region with high sensitivity.

The supporting member 202 may be formed by using a metallic material or the like having a high mechanical strength.

Each of the plurality of transducers 201 supported by the supporting member 202 receives acoustic waves and outputs a time-series reception signal.

Input Unit 103

The input unit 103 is a member configured to enable a user to designate desired information to input the information. As the input unit 103, a keyboard, a mouse, a touch panel display, a dial, a button, and the like may be used. In a case where a touch panel is used as the input unit 103, the display 109 may be a touch panel that also functions as the input unit 103. The input unit 103 may be provided separately from the photoacoustic apparatus according to this embodiment of the present invention.

Signal Processing Unit 105

The signal processing unit 105 is connected to the transducers 201 via signal lines, AD converts analog reception signals output from the transducers 201, and transmits the converted signals to the main controller 104. The signal processing unit 105 may be connected to a light detection sensor provided at the light exit 108, so as to obtain signals in synchronization with emission of pulsed light.

Light Irradiation Unit 106

The light irradiation unit 106 includes a light source that emits light, and an optical system that leads the light emitted from the light source to a subject.

The light source may be a pulsed light source capable of generating pulsed light of the order of nanoseconds to microseconds. Specifically, the pulsed light may have a pulse width of about 1 to 100 nanoseconds. Also, the pulsed light may have a wavelength in the range from about 400 nm to 1600 nm. In particular, in the case of imaging a blood vessel near the surface of a living body with high resolution, light having a wavelength in the visible range (400 nm or more and 700 nm or less) may be used. On the other hand, in the case of imaging a deep portion of a living body, light having a wavelength that is less likely to be absorbed in a background tissues of a living body (700 nm or more and 1100 nm or less) may be used. Alternatively, terahertz waves, microwaves, or radio waves may be used.

A specific example of the light source is a laser or a light-emitting diode. In the case of measurement using light beams of a plurality of wavelengths, a light source capable of converting an oscillation wavelength may be used. In the case of irradiating a subject with light beams of a plurality of wavelengths, a plurality of light sources that oscillate light beams of different wavelengths may be used by switching oscillation or alternately emitting the light beams. Even in a case where a plurality of light sources are used, they are collectively referred to as a light source.

As the laser, various types of lasers may be used, for example, a solid-state laser, a gas laser, a dye laser, and a semiconductor laser. In particular, a pulse laser such as an Nd:YAG laser or an alexandrite laser may be used. Alternatively, a Ti:sa laser or an optical parametric oscillation (OPO) laser that use Nd:YAG laser light as pumping light may be used.

The optical system causes pulsed light to travel from the light source to a subject. As the optical system, optical devices such as a lens, a mirror, and an optical fiber may be used. In a biological information obtaining apparatus that uses a breast or the like as a subject, a light emitter of an optical system may emit pulsed light that has a beam diameter extended by using a diffusion plate or the like. On the other hand, in a photoacoustic microscope, a light emitter of an optical system may be constituted by a lens or the like and emit light by focusing a beam diameter in order to increase resolution.

Alternatively, the light irradiation unit 106 does not include an optical system, and a subject may be directly irradiated with light emitted from the light source.

The light source of the light irradiation unit 106 according to this embodiment is connected to the light exit 108 via an optical fiber serving as the optical system. Pulsed light is emitted from the bottom of the supporting member 202 toward the curvature center of the hemispherical supporting member 202.

Driving Unit 107

The driving device 107 serving as a driving unit changes the relative positions of a subject and the supporting member 202. In this embodiment, the driving device 107 moves the supporting member 202 in the x- and y-directions, and includes an electric-powered XY stage on which a stepping motor is mounted. The driving device 107 is not limited to a device that two-dimensionally changes the relative positions of a subject and the supporting member 202, and a device that one-dimensionally or three-dimensionally changes the relative positions may be used.

The driving device 107 includes a guiding mechanism for a movement direction, a driving mechanism for a movement direction, and a position sensor that detects the position of the supporting member 202. In the case of the photoacoustic apparatus illustrated in FIG. 1, the supporting member 202 is mounted on the driving device 107, and thus a linear guide or the like resistant to a heavy load may be used as the guiding mechanism. As the driving mechanism, a lead screw mechanism, a link mechanism, a gear mechanism, a hydraulic mechanism, or the like may be used. A motor may be used as a driving force. As the position sensor, a potentiometer including an encoder, a variable resistor, and so forth may be used.

In an exemplary embodiment of the present invention, it is sufficient that the relative positions of a subject and the supporting member 202 are changed, and thus the supporting member 202 may be fixed and the subject may be moved. In the case of moving the subject, a subject supporting member for supporting the subject (not illustrated) may be moved to move the subject. Both of the subject and the supporting member 202 may be moved.

The movement may be continuously performed, or may be repeatedly performed in certain steps. The driving device 107 may be an electric-powered stage, or may be a manually-operated stage. The driving device 107 is not limited to the one described above, and any types of device may be used as long as it is configured to be able to move at least one of a subject and the supporting member 202.

Main Controller 104

The main controller 104 is connected to the input unit 103, the signal processing unit 105, the light irradiation unit 106, and the driving device 107 via a bus such as a universal serial bus (USB). The main controller 104 controls the individual devices, and typically is a built-in personal computer (PC). The main controller 104 reconstructs subject information, such as an initial sound pressure generated from a subject, by using a signal received from the signal processing unit 105. The main controller 104 includes a central processing unit (CPU) serving as a control unit. Also, the main controller 104 includes an arithmetic element such as a CPU or a graphics processing unit (GPU), and an arithmetic circuit such as a field-programmable gate array (FPGA) or an application specific integrated circuit (ASIC). Also, the main controller 104 includes a memory such as a read only memory (ROM), a random access memory (RAM), or a hard disk.

The function of the signal processing unit 105 may be implemented by the main controller 104. A combination of the main controller 104 and the signal processing unit 105 is regarded as a processing unit according to this embodiment. Individual functions of the processing unit may be implemented by a plurality of hardware units. Alternatively, the individual functions of the processing unit may be implemented by a single hardware unit. Alternatively, the individual functions of the processing unit may be implemented by different hardware units.

Display 109

The display 109 serving as a display unit displays subject information output from the main controller 104 in the form of a distribution image or numeric data. Typically, a liquid crystal display or the like is used as the display 109, but another type of display, such as a plasma display, an organic electroluminescence (EL) display, or a field emission display (FED), may be used. The display 109 may be provided separately from the photoacoustic apparatus according to an embodiment of the present invention.

Subject Information Obtainment Processing

Figure 3:
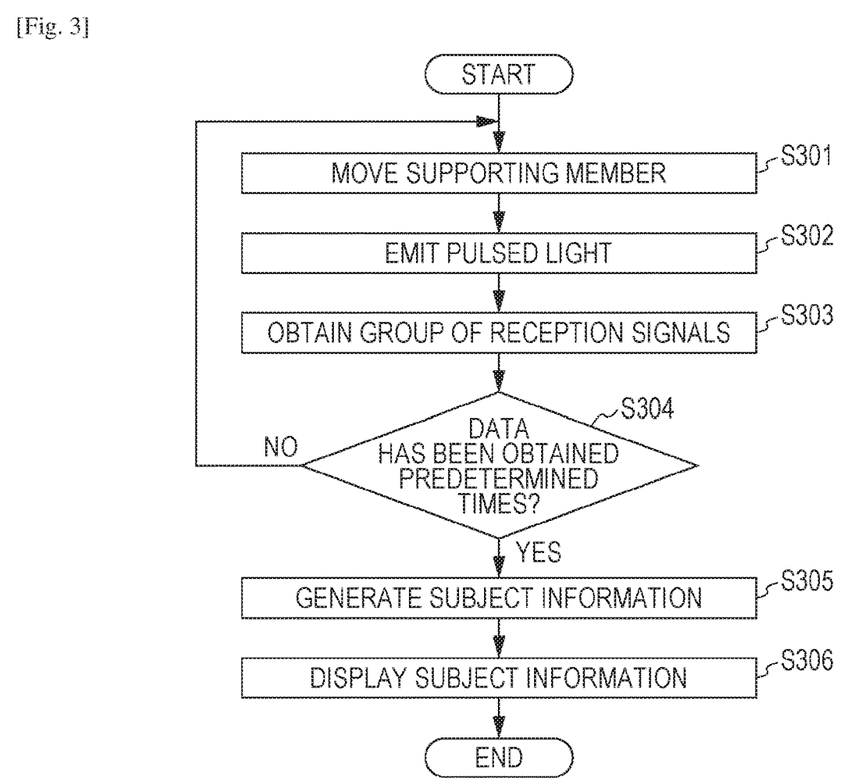
FIG. 3 is a flowchart illustrating processing according to the first embodiment.

Next, a detailed description will be given of the processing performed by the photoacoustic apparatus with reference to the flowchart illustrated in FIG. 3. The processing is performed by the main controller 104 which controls the individual units of the photoacoustic apparatus.

Upon start of the processing, the main controller 104 transmits an instruction to the driving device 107, and accordingly the driving device 107 moves the supporting member 202 to a predetermined irradiation position (step S301).

Subsequently, the main controller 104 transmits an instruction to the light irradiation unit 106, and accordingly the light irradiation unit 106 emits pulsed light, so that pulsed light is emitted from the light exit 108 (step S302). Subsequently, each of the plurality of transducers 201 receives photoacoustic waves and outputs a reception signal to the signal processing unit 105. At this time, the signal processing unit 105 starts, in synchronization with emission of pulsed light, signal processing for a group of reception signals. After that, the main controller 104 transmits an instruction to the signal processing unit 105, and accordingly the signal processing unit 105 transmits, to a first memory of the main controller 104, the group of reception signals on which signal processing has been performed (step S303). Here, an operation of obtaining data of a group of reception signals means an operation of converting a group of time-series reception signals output from the plurality of transducers 201 into digital signals and storing the digital signals in the first memory of the main controller 104.

In this embodiment, data of a group of reception signals is obtained a plurality of times by changing the relative positions of the holding cup 101 and the supporting member 202. Thus, the main controller 104 determines whether data of a group of reception signals has been obtained a predetermined times (step S304). If data of another group of signals is to be obtained, the processing returns to step S301. As a result, data of a plurality of groups of reception signals corresponding to a plurality of times of irradiation is stored in the first memory of the main controller 104.

After signals have been obtained the predetermined number of times, the main controller 104 generates subject information on the basis of the data of the plurality of groups of reception signals stored in the main controller 104 (step S305). The data of the groups of reception signals is data of time-series signals, and the subject information is spatial two-dimensional or three-dimensional data. Spatial two-dimensional data is also referred to as pixel data, and spatial three-dimensional data is referred to as voxel data or volume data. A pixel or a voxel corresponds to a target position according to this embodiment. That is, in this step, the main controller 104 performs reconstruction processing of converting data of the plurality of groups of reception signals into data of spatial subject information.

Finally, the main controller 104 displays the resulting subject information on the display 109 (step S306). In a typical case, images of cross sections taken along an XY plane, a YZ plane, and a ZX plane of three-dimensional subject information are displayed.

Figure 4:
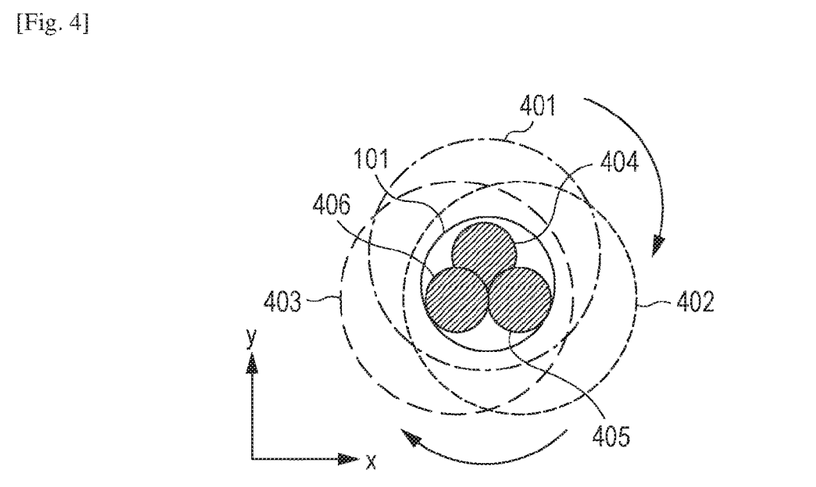
FIG. 4 is a diagram illustrating movements of a supporting member according to the first embodiment.

FIG. 4 is a diagram illustrating a state in which the driving device 107 moves the supporting member 202, viewed from the z-axis direction. Circles 401, 402, and 403 represent the positions of the supporting member 202 at a first timing, a second timing, and a third timing of obtaining signals (irradiation with light), respectively. At the time of obtaining signals in the circle 401, a region 404 is a highly-sensitive region. At the time of obtaining signals in the circle 402, a region 405 is a highly-sensitive region. At the time of obtaining signals in the circle 403, a region 406 is a highly-sensitive region. The movement method and signal obtainment timings (the number) are not limited to this example. For example, the driving device 107 may spirally move the supporting member 202 toward the center of the holding cup 101.

Reconstruction Processing

Figure 5:
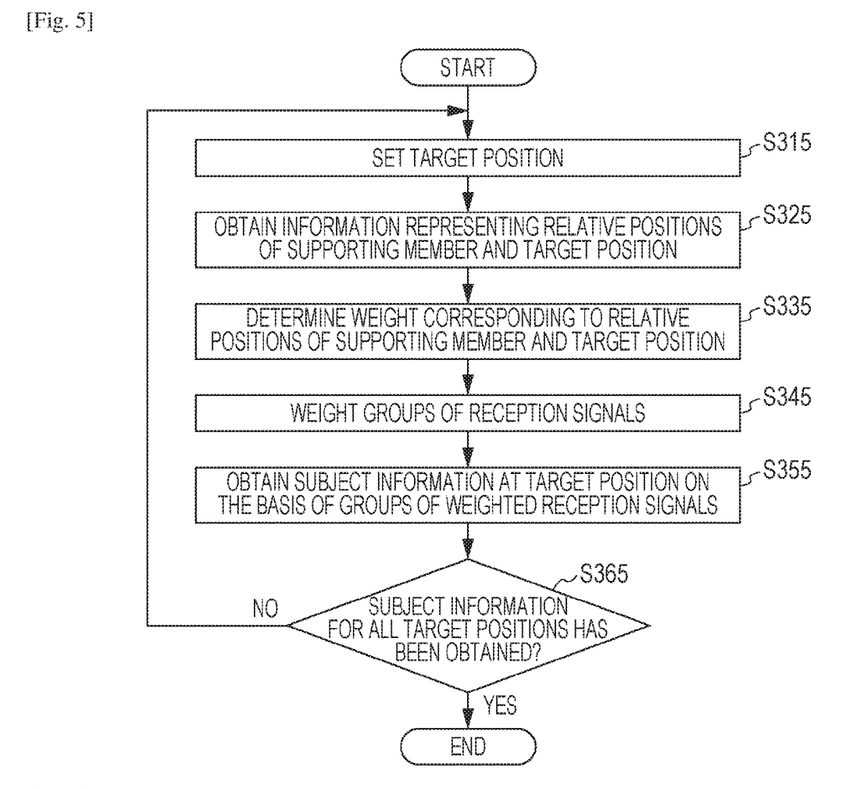
FIG. 5 is a flowchart illustrating signal processing according to the first embodiment.

A description will be given of a specific example of the reconstruction processing performed by the main controller 104 in step S305 with reference to the flowchart illustrated in FIG. 5.

In this embodiment, a weight corresponding to the relative positions of the supporting member and a target position is assigned to reception signal data obtained through a plurality of times of irradiation, so as to perform reconstruction processing.

The main controller 104 sets a target position for reconstruction, for example, a voxel (step S315). The set target position may be predetermined, or may be designated by a user using the input unit 103. The main controller 104 may set a target position on the basis of information representing the positions of the subject at individual irradiation timings. There is a probability that the position of the subject corresponding to the target position set before irradiation is changed when the subject is irradiated, and thus the target position for reconstruction may be changed in accordance with information representing the position of the subject at each irradiation timing. The photoacoustic apparatus may include a first measurement unit capable of measuring a position of a subject. As the first measurement unit, a device for measuring a position of a subject by using image data obtained from a charge-coupled device (CCD) camera, a complementary metal-oxide semiconductor (CMOS) camera, or the like, or a device for measuring a position of a subject by using information representing displacement of the subject obtained by a gyro sensor or the like may be used.

The main controller 104 obtains information representing the relative positions of the supporting member 202 and the target position when the subject is irradiated with pulsed light in step S302 (step S325).

The main controller 104 may include a second memory that stores in advance weights corresponding to the relative positions of the supporting member 202 and the target position at individual irradiation timings. The main controller 104 is able to read a weight corresponding to each irradiation from the second memory, and thereby determine the weight. The first memory and the second memory may be constituted by a single hardware unit or different hardware units.

The main controller 104 may receive information representing the positions of the supporting member 202 at the individual irradiation timings, the positions detected by the position sensor as a second measurement unit provided in the driving device 107. The second measurement unit may obtain information representing the position of the supporting member 202 by using, as a trigger, an irradiation control signal for the light irradiation unit 106 or light emitted from the light irradiation unit 106. Accordingly, even in a case where an error occurs between a preset irradiation timing or the position of the supporting member 201 and an actual measurement state, information representing the position of the supporting member 202 at the time when light is actually applied can be obtained with high accuracy.

The main controller 104 determines, on the basis of the position information about the target position obtained in step S315 and the position information about the supporting member 202 obtained in step S325, a weight corresponding to the relative positions of the target position and the supporting member 202 (step S335).

Figure 6:
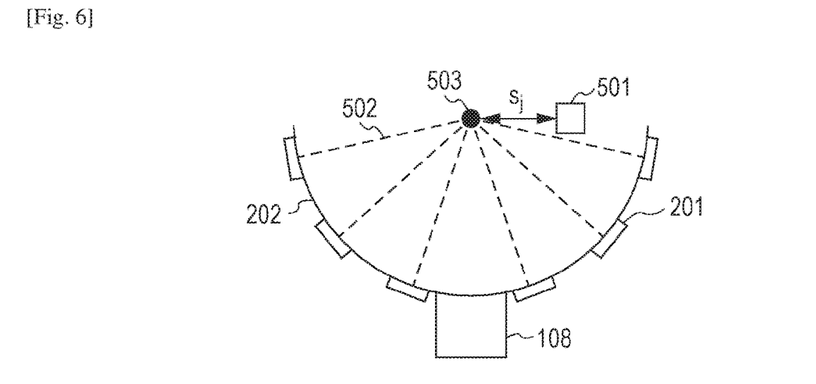
FIG. 6 is a diagram for describing an example of a weight according to the first embodiment.

Now, a specific example of a weight will be described with reference to FIG. 6. A voxel 501 as a target position is a voxel to be reconstructed. Broken lines 502 represent directional axes of the individual transducers 201. A point 503 is the curvature center of the supporting member 202 at the j-th irradiation. In this embodiment, the curvature center 503 corresponds to a position at which the directional axes of at least some of the plurality of transducers 201 converge. $s_j$ represents the distance between the voxel 501 and the curvature center 503. In this case, the weight may increase as the distance $s_j$ decreases, and the weight may decrease as the distance $s_j$ increases. For example, a weight w may be an exponential function in which the distance $s_j$ is as an exponent, as expressed by Equation (2).

[Math.2]

$$w_j = e^{-s_j^2} \qquad \text{Equation (2)}$$

An average of a plurality of weights adapted to the individual transducers 201 at the time when the supporting member 202 and the voxel 501 have a certain relative positional relationship may be used as a weight assigned to the individual transducers 201. For example, an average of weights adapted to individual transducers 201 used for reconstructing an image in the time domain called Universal Back Projection (UBP) described in Xu, Minghua, and Lihong V. Wang. "Universal back-projection algorithm for photoacoustic computed tomography" Physical Review E 71.1 (2005) may be used as a weight. In the case of UBP, a weight $w_{i,j}$ corresponding to the transducer at the position represented by a position vector $d_{i,j}$ (the position vector of the i-th transducer at the j-th irradiation) is expressed by Equation (3).

[Math. 3]

$$w_{i,j} = \frac{\Delta S_{i,j}}{|r - d_{i,j}|^2} \cdot \left[ n_{0i,j}^s \cdot \frac{(r - d_{i,j})}{|r - d_{i,j}|} \right] \qquad \text{Equation (3)}$$

Here, $\Delta S_{i,j}$ represents the area of the transducer existing at the position represented by the position vector $d_{i,j}$, and $ns_{0i,j}$ represents a unit normal vector (orientation direction) with respect to the reception surface of the transducer existing at the position represented by the position vector $d_{i,j}$. That is, a weight adapted to each transducer in UBP is a solid angle of each transducer with respect to a voxel.

In this case, a weight $w_j$ to be assigned to each transducer 201 supported by the supporting member 202 at the j-th irradiation can be expressed by equation (4) by averaging weights $w_{i,j}$ of the individual transducers 201.

[Math. 4]

$$w_j = \frac{\sum_{i=1}^{N} \left( \frac{\Delta S_{i,j}}{|r - d_{i,j}|^2} \cdot \left[ n_{0i,j}^s \cdot \frac{(r - d_{i,j})}{|r - d_{i,j}|} \right] \right)}{N} \qquad \text{Equation (4)}$$

Alternatively, weights adapted to the individual transducers 201 used for image reconstruction according to the related art may be averaged, and the average weight may be used. In the case of using the average weight, the average weight may be stored in the second memory, and may be read from the second memory at the time of reconstruction.

Figure 7A:
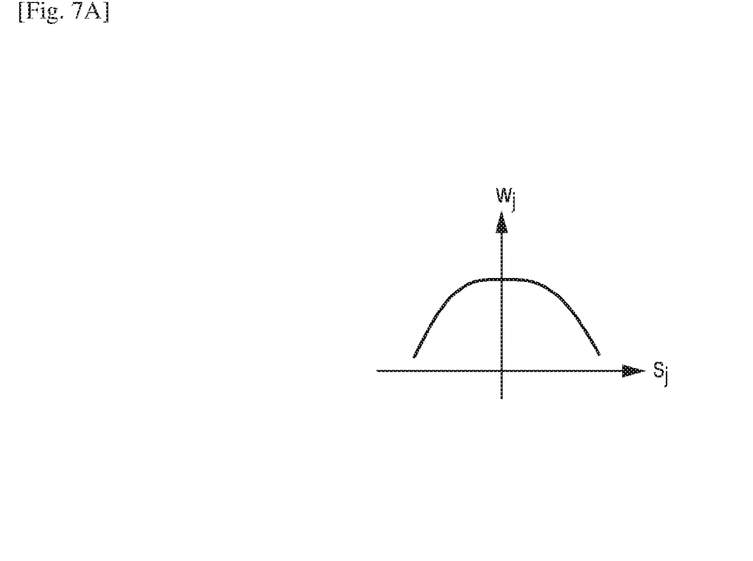
FIG. 7A is a diagram illustrating an example of a weight according to the first embodiment.
Figure 7B:
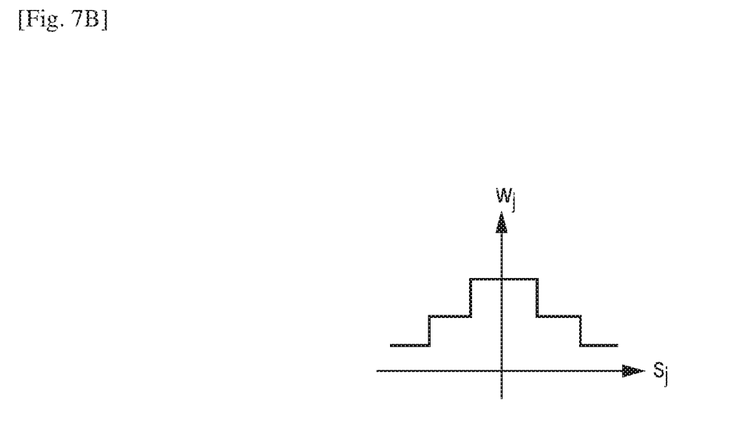
FIG. 7B is a diagram illustrating an example of a weight according to the first embodiment.

The main controller 104 may change the weight step by step in accordance with the distance $s_j$. For example, the main controller 104 may continuously change the weight as illustrated in FIG. 7A, or may discretely change the weight as illustrated in FIG. 7B.

The value of a weight is not limited to the above-described example, and any value of a weight may be used as long as the weight can be uniformly assigned to the individual transducers on the basis of the positional relationship between the supporting member and the target position. Alternatively, the main controller 104 may calculate a weight by using Equation (2) or Equation (4). Alternatively, a correspondence table of distances $s_j$ and weights w may be created and stored in the second memory of the main controller 104 in advance, and the main controller 104 may read a weight $w_j$ corresponding to a distance $s_j$ with reference to the correspondence table at the time of reconstruction processing.

Now, a description will be given of the reason why a weight may be increased as the distance $s_j$ between the target position for reconstruction and the curvature center of the supporting member 202 decreases.

In this embodiment, the transducers 201 have directivity and are fixed toward the center of the hemisphere. Thus, acoustic waves generated at the vicinity of the center of the hemisphere can be received by the individual transducers 201 with high sensitivity. In general, in the case of reconstructing a certain sound source, the reconstruction can be performed with higher resolution by receiving acoustic waves in the direction for covering the largest possible solid angle. In this case, acoustic waves from the center of the hemisphere can be received with high sensitivity at the largest solid angle, and thus the weight may be increased toward the center of the hemisphere to perform reconstruction.

A larger weight may be assigned to a group of reception signals output from a plurality of transducers when the initial sound pressure of the acoustic waves generated at the target position is high. For example, a large weight may be assigned to a group of reception signals of acoustic waves generated when the fluence of light applied to the target position is high. That is, a weight corresponding to the amount of light may be applied to data of a group of reception signals. Accordingly, a weight for a group of reception signals having a high S/N ratio can be increased. Thus, the S/N ratio of subject information at the target position reconstructed by using the group of weighted reception signals can also be increased. For example, a value calculated by multiplying a weight determined in accordance with the relative positions of the supporting member and the target position by the amount of light at the target position may be used as a weight.

In a case where pulsed light is emitted toward the center of the hemisphere as in this embodiment, the sound pressure of photoacoustic waves generated at the center of the hemisphere relatively increases. In this case, in the vicinity of the center of the hemisphere, a region where a generated sound pressure of photoacoustic waves is high and a region where the generated photoacoustic waves are received with high sensitivity overlap each other, and thus a large weight may be assigned to perform reconstruction. For this reason, the light irradiation unit 106 may emit pulsed light toward the position at which directional axes of a plurality of transducers converge.

Figure 8A:
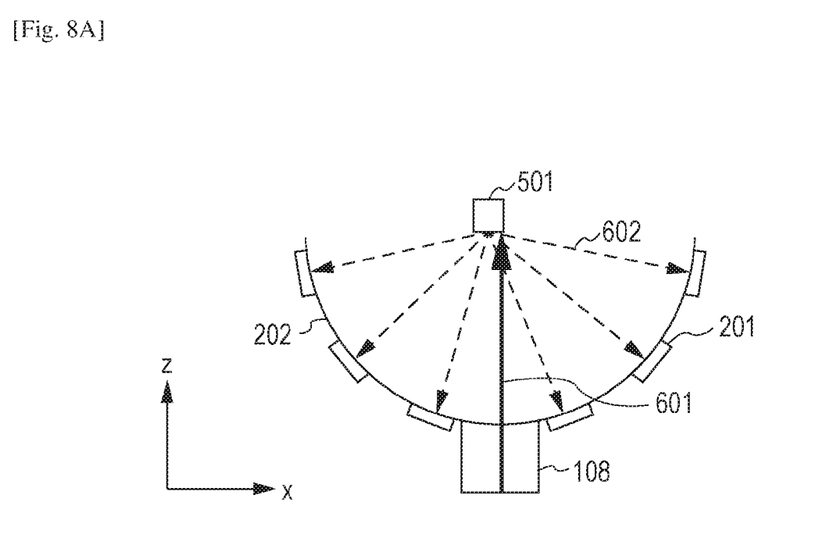
FIG. 8A is a diagram illustrating propagation of pulsed light and acoustic waves according to the first embodiment.
Figure 8B:
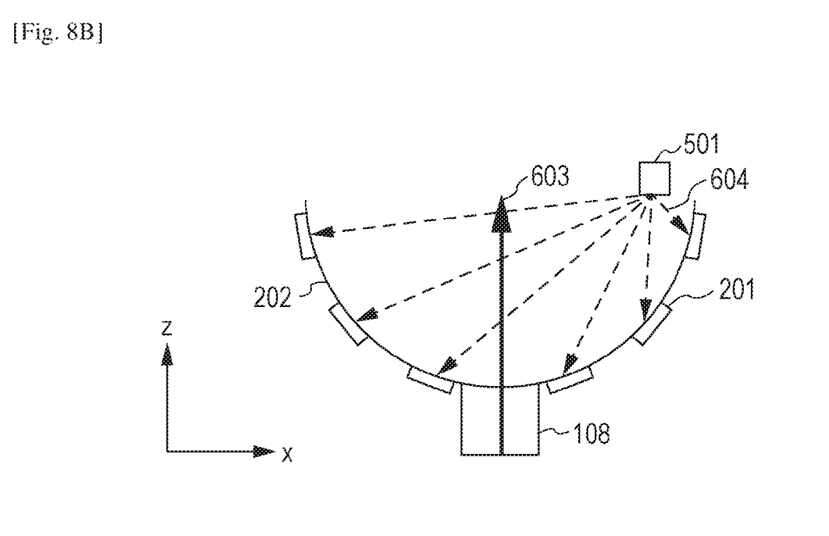
FIG. 8B is a diagram illustrating propagation of pulsed light and acoustic waves according to the first embodiment.

FIGS. 8A and 8B are diagrams illustrating a state of pulsed light emitted from the light exit 108 and a state where acoustic waves output from the voxel 501 reach the transducers 201. Acoustic waves may be output from a position other than the voxel 501, but the illustration thereof is omitted for convenience.

FIG. 8A is a diagram illustrating a case where the distance $s_j$ is short. Pulsed light 601 is intensely applied to the voxel 501, and intense acoustic waves 602 are output from the voxel 501. The acoustic waves 602 enter the individual transducers 201 at almost the right angles. Thus, the individual transducers 201 obtain reception signals that largely contribute to increase the quantitativity of subject information of the voxel 501 to be obtained.

On the other hand. FIG. 8B is a diagram illustrating a case where the distance $s_j$ is long. Pulsed light 603 is hardly applied to the voxel 501, and accordingly the intensity of acoustic waves 604 output from the voxel 501 is low. Further, the acoustic waves 604 enter many of the transducers 201 at an angle with respect to a perpendicular direction on the reception surface. Thus, the individual transducers 201 dominantly obtain reception signals that do not largely contribute to increase the quantitativity of subject information of the voxel 501 to be obtained.

Accordingly, it is understood that a group of obtained reception signals contribute more largely to increase the quantitativity of subject information of the voxel 501 as the distance s decreases, and thus a large weight may be assigned to the group of reception signals.

As described above, the position of the curvature center of the supporting member 202 and the position at which the directional axes of the plurality of transducers 202 converge can be estimated on the basis of the position of the supporting member 202. Thus, a weight may be determined with reference to the positional relationship between the supporting member 202 and a target position.

In this step, in a case where a weight is determined on the basis of information representing the position of a subject measured by the first measurement unit and information representing the position of the supporting member 202 measured by the second measurement unit, the relative positions of the supporting member 202 and the subject at the time when light is actually applied can be determined with high accuracy. Thus, a weight that is suitable for an actual state at the time of irradiation and that corresponds to the relative positions of the supporting member 202 and the target position can be determined.

The main controller 104 assigns the weight determined in step S335 to each of the plurality of groups of reception signals stored in the first memory (step S345). Subsequently, the main controller 104 obtains subject information at the target position on the basis of the plurality of groups of weighted reception signals (step S355).

Now, a specific example of steps S345 and S355 will be described. The position vector of a voxel to be reconstructed (target position) is represented by r, the initial sound pressure of the voxel to be reconstructed is represented by $p_0(r)$, the number of transducers 201 is represented by N, the number of times signal data is obtained (the number of times of irradiation) is represented by M, and the sonic speed of acoustic waves in a propagation path is represented by c. Also, a weight assigned to data of a group of reception signals at the time of the j-th irradiation is represented by $w_j$ (j is larger than or equal to 1 and smaller than or equal to M), the position vector of the i-th transducer at the time of the j-th irradiation is represented by $d_{i,j}$, and a signal strength at time t' of data of time-series reception signals obtained by the transducer at the position represented by the position vector $d_{i,j}$ is represented by $p(d_{i,j}, t')$. In this case, for example, the main controller 104 is able to calculate an initial sound pressure as subject information by using the equation expressed by Equation (5).

[Math. 5]

$$p_0(r) = \sum_{j=1}^{M} \left( w_j \sum_{i=1}^{N} p\left(d_{i,j}, t' = \frac{|d_{i,j} - r|}{c}\right) \right)$$

Equation (5)

The main controller 104 determines whether or not subject information for all the set target positions has been obtained (step S365). If subject information for all the set target positions has not been obtained, the processing returns to step S315. The step that has been performed for all the target positions need not be performed again. That is, the processing may return to the step that has not been performed for all the target positions. Equation (5) expresses only a case where one certain voxel is reconstructed. With the same processing repeatedly performed on a plurality of voxels (all the target positions), a certain region can be reconstructed.

The main controller 104 may calculate initial sound pressures for data of groups of reception signals obtained through the first to j-th irradiations by using Equation (6), and then may combine the initial sound pressures.

[Math. 6]

$$p_0(r) = w_j \sum_{i=1}^{N} p\left(d_{i,j}, t' \frac{|d_{i,j} - r|}{c}\right)$$

Equation (6)

That is, step S305 may be performed to obtain subject information every time steps S301 to S303 are performed. A plurality of pieces of subject information obtained in step S305 may be combined to obtain final subject information. Regarding a reception signal $p(d_{i,j}, t')$ to which a weight is assigned, the weight may be assigned after the reception signal $p(d_{i,j}, t')$ has been positively defined as expressed by Equation (7), as described in Xu, Minghua, and Lihong V. Wang. "Universal back-projection algorithm for photoacoustic computed tomography" Physical Review E 71.1 (2005).

[Math. 7]

$$b(d_{i,j}, t') = 2p(d_{i,j}, t') - 2t' \frac{\partial p(d_{i,j}, t')}{\partial t} \quad \text{Equation (7)}$$

Here, $b(d_{i,j}, t')$ represents the strength of the positively defined reception signal. An algorithm of positively defining the reception signal is not limited to Equation (7), and any other methods may be used.

In this embodiment, a description has been given of a weight that is based on the tendency for image quality to isotropically decrease from the curvature center of the supporting member. Alternatively, a weight that is based on a different tendency may be used. In a case where it is impossible to arrange transducers on a perfect spherical surface without gaps therebetween, a highly-sensitive region is not a sphere whose center is a position at which the directional axes of a plurality of transducers converge. In this case, there is a tendency in which higher image quality can be obtained in a region near the supporting member than in a region distant from the supporting member relative to the position at which the directional axes of the plurality of transducers converge. That is, in this case, the highly-sensitive region has a tendency to extend more in the region near the supporting member than in the region distant from the supporting member relative to the position at which the directional axes of the plurality of transducers converge.

On the basis of this tendency, the main controller may assign a weight to a target position included in the region near the supporting member, the weight being larger than a weight assigned to a target position included in the region distant from the supporting member, relative to the position at which the directional axes of the plurality of transducers converge. That is, among target positions at the same distance from the position at which the directional axes of the plurality of transducers converge, a weight may be assigned to a target position included in the region near the supporting member, the weight being larger than a weight assigned to a target position included in the region distant from the supporting member. Further, the main controller may assign the largest weight to a target position located on the probe side relative to the position at which the directional axes of the plurality of transducers converge. Further, the main controller may assign a larger weight as the distance from a certain position near the supporting member to a target position decreases, relative to the position at which the directional axes of the plurality of transducers converge. Also in these cases, a weight can be assigned on the basis of the relative positions of the supporting member and the target position.

According to this embodiment, a uniform weight corresponding to the positional relationship between a supporting member and a target position is assigned to a group of reception signals obtained from a plurality of transducers, and accordingly subject information having high quantitativity and resolution can be obtained.

Second Embodiment

The system configuration of a photoacoustic apparatus and subject information obtainment processing according to a second embodiment are similar to those according to the first embodiment. In this embodiment, a group of reception signals to be used for reconstructing a target position is selected from data of a plurality of groups of reception signals stored in the first memory. In other words, a group of reception signals not to be used for reconstruction is selected from among a plurality of groups of reception signals. At this time, a weight of 0 may be assigned to the group of reception signals not to be used for reconstruction, or the group of reception signals is not read at the time of reconstruction.

In photoacoustic imaging, signals to be used for reconstructing an image at a target position may be selected from the viewpoint described below.

An image at a target position may be reconstructed by using reception signals output from transducers whose directional axes are oriented to the target position. Accordingly, acoustic waves generated at the target position can be received with high sensitivity, and thus the S/N ratio of the reception signals corresponding to acoustic waves generated at the target position can be increased. Thus, the S/N ratio of the image strength at the target position reconstructed by using the reception signals can be increased.

In a case where a sound source exists at the target position, acoustic waves isotropically propagate from the target position to all directions. Thus, the transducers may be arranged so as to receive many frequency components of acoustic waves generated from the target position. Accordingly, at the time of reconstructing an image, the energy corresponding to a reconstruction artifact is distributed over the entire reconstructed image, and thus local occurrence of a reconstruction artifact can be suppressed.

Further, the transducers may receive acoustic waves at such positions that a reconstruction artifact symmetrically appears with the target position at the center. That is, the transducers may receive acoustic waves at point-symmetric positions with the target position at the center. Accordingly, a reconstruction artifact appears point-symmetrically with the target position at the center. As a result, the energy corresponding to the reconstruction artifact is distributed more evenly over the entire reconstructed image, and thus local occurrence of a reconstruction artifact is less likely to occur.

An image may be reconstructed by using reception signals based on the above-descried viewpoint at every target position. Accordingly, at every target position in the reconstructed image, the contrast between the reconstructed image at the target position (signal component) and a reconstruction artifact (noise component) is increased.

The photoacoustic apparatus according to this embodiment determines a group of reception signals to be used for obtaining subject information at a target position from among a plurality of groups of reception signals stored in the first memory in accordance with the relative positions of the supporting member and a target position. That is, the photoacoustic apparatus according to this embodiment determines a group of reception signals not to be used for obtaining subject information at the target position from among the plurality of groups of reception signals stored in the first memory in accordance with the distance between the supporting member and the target position.

For example, in step S335, the weight according to this embodiment is determined by using Equation (8).

[Math. 8]

$$w_j = \begin{cases} 1 & (s_j \leq d_{th}) \\ 0 & (s_j > d_{th}) \end{cases} \quad \text{Equation (8)}$$

Here, $d_{th}$ represents the radius of a highly-sensitive region. That is, a voxel is reconstructed without using, for calculation, a group of reception signals obtained at the time when the voxel is not included in a highly-sensitive region. The range of the highly-sensitive region as a threshold can be estimated by using Equation (1).

In this embodiment, a group of reception signals to be used for obtaining subject information is selected by using the radius of a highly-sensitive region as a threshold, but the threshold is not limited thereto.

As described above, the highly-sensitive region is not always a sphere whose center is a position at which the directional axes of the plurality of transducers 201 converge. The inventors have found that the highly-sensitive region may have a larger area in a region on the supporting member 202 side than in a region distant from the supporting member 202, relative to the position at which the directional axes of the plurality of transducers 201 converge. In this case, the main controller 104 may perform reconstruction for a target position at a further position in the direction of approaching the supporting member 202 relative to the position at which the directional axes of the plurality of transducers 201 converge, compared to the direction of becoming distant from the supporting member 202. The main controller 104 may perform reconstruction for only a target position at a closer position in the direction of becoming distant from the supporting member 202 relative to the position at which the directional axes of the plurality of transducers 201 converge, compared to the direction of approaching the supporting member 202. The main controller 104 may perform reconstruction for a target position at a position in the direction of approaching the supporting member 202, and need not perform reconstruction for a target position at a position in the direction of becoming distant from the supporting member 202, among target positions at the same distance from the position at which the directional axes of the plurality of transducers 201 converge.

Further, a certain region based on the position of the supporting member 202 may be reconstructed, and the other region need not be reconstructed. That is, the weight for a target position included in the region other than the certain region may be zero. Examples of the certain region may be a sphere whose center is the position at which the directional axes of a plurality of transducers supported by a supporting member converge, a circular column, and a square column. In this case, the distance from the position at which the directional axes of the plurality of transducers converge to the outer periphery of the certain region may be used as a threshold. As described above, in a case where the highly-sensitive region extends toward the supporting member 202, the center of the certain region may be offset to the supporting member 202 side relative to the position at which the directional axes of the plurality of transducers converge. Parameters for determining the certain region, such as a shape, size, and position, may be set in advance. A user may input a parameter for determining the certain region as information about a threshold by using the input unit 103, so as to set the threshold.

The threshold may vary depending on a direction from the position at which the directional axes of the plurality of transducers converge toward the target position.

The weight for a voxel to be reconstructed is not limited to 1, and another weight other than 0 may be used. Subject information can be obtained in accordance with an image reconstruction algorithm according to the related art, such as UBP, on the basis of a selected group of reception signals to be used for reconstruction. That is, a uniform weight corresponding to the relative positions of the supporting member 202 and the voxel 501 may be assigned to each reception signal included in a group of reception signals, and a weight corresponding to the relative positions of the individual positions of the plurality of transducers 201 and the voxel 501 may be assigned to each reception signal.

In this way, a group of reception signals to be used for reconstruction is selected from among a plurality of groups of reception signals, and thereby the amount of calculation performed for obtaining subject information can be reduced. Accordingly, the time for obtaining the subject information can be shortened. Also, a group of reception signals obtained at the time when the voxel to be reconstructed is not included in a highly-sensitive region is a group of reception signals that is not received with high sensitivity. Thus, if the group of reception signals is used for obtaining subject information, the quantitativity of the subject information may decrease. Thus, the group of reception signals is not used for obtaining subject information, and thereby the quantitativity and resolution of obtained subject information can be increased.

Modification Example

The above-described embodiments are examples for describing the present invention. The present invention can be implemented by appropriately changing or combining the above-described embodiments without deviating from the gist of the present invention.

The reconstruction processing to which the present invention is applicable is not limited to processing performed by using the above-described equations, and other time-domain reconstruction may be applied. Also, the present invention is applicable to Fourier-domain reconstruction and model base reconstruction.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiments of the present invention, and by a method performed by the computer of the system or apparatus by, for example, reading out and executing the computer executable instructions from the storage medium to perform the functions of one or more of the above-described embodiments. The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD) (registered trademark)), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of U.S. Patent Application No. 61/992,983, filed May 14, 2014, which is hereby incorporated by reference herein in its entirety.

The invention claimed is:

1. A photoacoustic apparatus comprising:
  a light irradiation unit configured to irradiate a subject with light;
  a plurality of transducers configured to receive acoustic waves generated in response to irradiation of the subject with light emitted from the light irradiation unit and output a group of reception signals in association with one time of light irradiation;
  a supporting member configured to support the plurality of transducers such that directional axes of at least some of the plurality of transducers converge;
  a driving unit configured to move at least one of the supporting member and the subject;
  a first memory configured to store the group of reception signals output from the plurality of transducers; and
  a processing unit configured to obtain relative positions of the supporting member and a target position in association with the one time of light irradiation and subject information at the target position,
  wherein the processing unit determines a weight for the group of reception signals on the basis of the relative positions such that reception signals in the group stored in the first memory are weighted by the determined weight uniformly.

2. The photoacoustic apparatus according to claim 1, wherein
  the supporting member has a shape that is based on a sphere, and
  a position at which the directional axes converge is a curvature center of the shape that is based on the sphere.

3. The photoacoustic apparatus according to claim 2, wherein the supporting member has a hemispherical shape as the shape that is based on the sphere.

4. The photoacoustic apparatus according to claim 1, wherein the light irradiation unit emits light toward the position at which the directional axes converge.

5. The photoacoustic apparatus according to claim 1, further comprising:
  a first measurement unit configured to measure information about a position of the supporting member in a plurality of states; and
  a second measurement unit configured to measure information about a position of the supporting member in the plurality of states,
  wherein the processing unit determines the weight on the basis of the position of the subject measured by the first measurement unit and the information about the position of the supporting member measured by the second measurement unit.

6. The photoacoustic apparatus according to claim 1, further comprising:
  a second memory that stores a plurality of weights corresponding to the relative positions of the supporting member and the target position in a plurality of states,
  wherein the processing unit determines the weight by reading a weight from the second memory.

7. The photoacoustic apparatus according to claim 1, wherein the weight assigned by the processing unit to each group of a plurality of groups of reception signals stored in the first memory is an exponential function that uses the distance as an exponent.

8. The photoacoustic apparatus according to claim 1, wherein the processing unit obtains the subject information at the target position without using, among a plurality of groups of reception signals stored in the first memory, a group of reception signals output from the plurality of transducers is longer than a threshold.

9. The photoacoustic apparatus according to claim 8, wherein the threshold varies depending on a direction from the position at which the directional axes converge toward the target position.

10. The photoacoustic apparatus according to claim 8, wherein the processing unit sets, as the threshold, a distance from the position at which the directional axes converge to a position at which a resolution is half of a maximum resolution, the maximum resolution being obtained at the position at which the directional axes converge.

11. The photoacoustic apparatus according to claim 10, wherein the processing unit increases the weight assigned to each of the plurality of groups of reception signals stored in the first memory as the distance decreases.

12. The photoacoustic apparatus according to claim 8, further comprising:
  an input unit configured to enable information about the threshold to be input,
  wherein the processing unit sets the threshold on the basis of information about the threshold output from the input unit.

13. The photoacoustic apparatus according to claim 1, wherein the processing unit assigns, for target positions included in a certain region on the basis of a position of the supporting member, 0 as the weight.

14. The photoacoustic apparatus according to claim 1, wherein the processing unit assigns, to each of tho a plurality of groups of reception signals stored in the first memory, a weight which is an average of weights adapted to the plurality of transducers.

15. The photoacoustic apparatus according to claim 1, wherein the processing unit assigns, to each reception signal included in a group of reception signals, a uniform weight corresponding to the relative positions of the supporting member and the target position and a fluence of light applied to the target position.

16. The photoacoustic apparatus according to claim 1, wherein the processing unit assigns, to each reception signal included in a group of reception signals, a uniform weight corresponding to the relative positions of the supporting member and the target position and a weight corresponding to relative positions of individual positions of the plurality of transducers and the target position.

17. A signal processing method for obtaining subject information at a target position of a subject by using a plurality of transducers arranged on a supporting member such that directional axes of at least some of the plurality of transducers converge, in a plurality of states where relative positions of the supporting member and the subject differ, on the basis of a plurality of groups of reception signals that have been obtained by receiving acoustic waves generated from the subject and stored, and that correspond to the plurality of states, the signal processing method comprising:
- a step of obtaining relative positions of the supporting member and the target position in association with a timing of the plurality of times of light irradiation;
- a step of determining a uniform weight for each of the plurality of stored groups of reception signals on the basis of the relative positions;
- a step of weighting each of the plurality of stored groups of reception signals by the uniform weight; and
- a step of obtaining subject information based on the weighted groups of reception signals corresponding to the target position.

18. A non-transitory storage medium storing a program that causes a computer to execute the signal processing method according to claim 17.

19. A signal processing apparatus for obtaining subject information at a target position of a subject by using a plurality of transducers arranged on a supporting member such that directional axes of at least some of the plurality of transducers converge, in a plurality of states where relative positions of the supporting member and the subject differ, on the basis of a plurality of groups of reception signals that have been obtained by receiving acoustic waves generated from the subject and stored, and that correspond to the plurality of states, the signal processing apparatus comprising:
- a first memory configured to store the group of reception signals output from the plurality of transducers; and
- a processing unit configured to perform:
  - a step of obtaining relative positions of the supporting member and the target position in association with a timing of the plurality of times of light irradiation;
  - a step of determining a uniform weight for each of the plurality of stored groups of reception signals on the basis of the relative positions;
  - a step of weighting each of the plurality of stored groups of reception signals by the uniform weight; and
  - a step of obtaining subject information based on the weighted groups of reception signals corresponding to the target position.

20. The signal processing apparatus according to claim 19, wherein the processing unit obtains the subject information at the target position without using, among the plurality of groups of reception signals, a group of reception signals output from the plurality of transducers is longer than a threshold.

21. The signal processing apparatus according to claim 20, wherein the threshold varies depending on a direction from the position at which the directional axes converge toward the target position.

22. The photoacoustic apparatus according to claim 20, wherein the processing unit sets, as the threshold, a distance from the position at which the directional axes converge to a position at which a resolution is half of a maximum resolution, the maximum resolution being obtained at the position at which the directional axes converge.

23. The signal processing apparatus according to claim 22, wherein the processing unit increases the weight assigned to each of the plurality of groups of reception signals stored in the first memory as the distance decreases.

24. The photoacoustic apparatus according to claim 20, further comprising:
- an input unit configured to enable information about the threshold to be input,
- wherein the processing unit sets the threshold on the basis of information about the threshold output from the input unit.

25. The photoacoustic apparatus according to claim 19, wherein the processing unit assigns, for target positions included in a certain region on the basis of a position of the supporting member, 0 as the weight.

* * * * *